United States Patent
Ellis-Grosse

(10) Patent No.: US 11,541,064 B2
(45) Date of Patent: Jan. 3, 2023

(54) METHODS OF IDENTIFYING DOSING REGIMENS

(71) Applicant: Zavante Therapeutics, Inc., San Diego, CA (US)

(72) Inventor: Evelyn Ellis-Grosse, San Diego, CA (US)

(73) Assignee: Zavante Therapeutics, Inc., San Diego, CA (US)

( * ) Notice: Subject to any disclaimer, the term of this patent is extended or adjusted under 35 U.S.C. 154(b) by 245 days.

(21) Appl. No.: 16/618,037

(22) PCT Filed: May 30, 2018

(86) PCT No.: PCT/US2018/035035
§ 371 (c)(1),
(2) Date: Nov. 27, 2019

(87) PCT Pub. No.: WO2018/222656
PCT Pub. Date: Dec. 6, 2018

(65) Prior Publication Data
US 2020/0253992 A1    Aug. 13, 2020

Related U.S. Application Data

(60) Provisional application No. 62/512,655, filed on May 30, 2017, provisional application No. 62/567,599, filed on Oct. 3, 2017, provisional application No. 62/582,880, filed on Nov. 7, 2017.

(51) Int. Cl.
*A61P 31/04* (2006.01)
*A61K 31/665* (2006.01)
*A61K 9/00* (2006.01)

(52) U.S. Cl.
CPC ............ *A61K 31/665* (2013.01); *A61P 31/04* (2018.01); *A61K 9/0019* (2013.01)

(58) Field of Classification Search
CPC ....................................................... A61P 31/04
See application file for complete search history.

(56) References Cited

U.S. PATENT DOCUMENTS

| 2010/0063005 A1 | 3/2010 | Fiala |
| 2015/0132382 A1 | 5/2015 | Dedhiya et al. |
| 2016/0346354 A1 | 12/2016 | Heslet et al. |

FOREIGN PATENT DOCUMENTS

| JP | 5750919 | | 3/1982 |
| JP | S5750919 A | * | 3/1982 |

OTHER PUBLICATIONS

Written Opinion for PCT/US2018/035035. (dated Jun. 12, 2018). (Year: 2018).*
VanScoy, Brian D., et al. "Exploration of the Pharmacokinetic-Pharmacodynamic Relationships for Fosfomycin Efficacy Using an In Vitro Infection Model." Antimicrobial Agents and Chemotherapy. (Dec. 2015), vol. 59, No. 12, pp. 7170-7177. (Year: 2015).*
Pruekprasert et al., "In vitro activity of fosfomycin-gentamicin, fosfomycin-ceftazidime, fosfomycin-imipenem and ceftazidime-gentamicin combinations against ceftazidime-resistant pseudomonas aeruginosa." (Sep. 2005) Southeast Asian J Trop Med Public Health, 36(5).
Okazaki et al., "Effectiveness of fosfomycin combined with other antimicrobial agents against multidrug-resistant Pseudomonas aeruginosa isolates using the efficacy time index assay." (2002) J Infect Chemother 8:37-42, p. 40, Table 3.
Kastoris et al., "Synergy of fosfomycin with other antibiotics for Gram-positive and Gram-negative bacteria." (2010) Eur J Clin Pharmacol 66:359-368, p. 366, Table 3.
Wikipedia, "Nephrotoxicity", Jan. 7, 2017 (Jan. 7, 2017), retrieved on Sep. 14, 2018 from https://en.wikipedia.org/w/index.php?title=Nephrotoxicity&oldid=758775998; entire document, especially p. 2 para 7.
Nagel et al., "Clinical efficacy of fosfomycin for the treatment of complicated lower tract and uncomplicated urinary tract infections," vol. 8 No. 151 doi: 10.3823/1750, (2015); entire document, especially abstract.

* cited by examiner

*Primary Examiner* — John S Kenyon
(74) *Attorney, Agent, or Firm* — Lewis Kohn & Walker LLP; David M. Kohn

(57) ABSTRACT

Methods for identification of new dosing strategies which optimize positive treatment outcomes and patient safety. Specifically, new dosing strategies for fosfomycin and pharmaceutically acceptable salt thereof which have improved treatment outcomes in mammals. For example, a method of treating mammals having a bacterial infection with fosfomycin or a pharmaceutically acceptable salt thereof using improved dosing regimens.

9 Claims, 6 Drawing Sheets

| | | ZTI-01 | P-T |
|---|---|---|---|
| Patients randomized (ITT) | N= 465 | 233 (100%) | 232 (100%) |
| Patients receiving ≥ 1 dose study drug (MITT, safety population) | N= 464 | 233 (100%) | 231 (99.6%) |
| Patients meeting clinical eligibility (CE-TOC) subset of MITT + I/E criteria + min 9 doses + w/in window visits | N= 395 | 199 (85.4%) | 196 (84.5%) |
| Patients who have at least 1 gram negative pathogen ≥ 10⁵ CFU/mL (m-MITT, subset of MITT, Primary Endpoint) | N= 362 | 184 (79%) | 178 (76.7%) |
| Patients meeting microbiologic evaluability at TOC (ME, subset of m-MITT and CE + results w/in TOC visit window) | N= 300 | 155 (66.5%) | 145 (62.5%) |

FIG. 4

METHODS OF IDENTIFYING DOSING REGIMENS

CROSS REFERENCE TO RELATED APPLICATIONS

This application is a U.S. national phase application under 35 U.S.C. § 371 claiming priority to International Application No. PCT/US2018/035035 filed May 30, 2018, which claims the benefit of priority from U.S. Provisional Patent Application No. 62/512,655 filed May 30, 2017, U.S. Provisional Patent Application No. 62/567,599 filed Oct. 3, 2017, and U.S. Provisional Patent Application No. 62/582,880 filed Nov. 7, 2017.

FIELD OF THE INVENTION

The present invention provides methods for identification of new dosing strategies which optimize positive treatment outcomes and patient safety. Specifically, the present invention provides new dosing strategies for fosfomycin and pharmaceutically acceptable salt thereof which have improved treatment outcomes in mammals. For example, the present invention provides a method of treating mammals having a bacterial infection with fosfomycin or a pharmaceutically acceptable salt thereof using improved dosing regimens. The present invention reduces the emergence of resistance and increases the effectiveness against resistant strains.

BACKGROUND OF THE INVENTION

Fosfomycin, a phosphonic acid derivative, acts by disrupting cell wall synthesis and exhibits bactericidal activity against anaerobic pathogens (including both Gram-positive and Gram-negative bacteria), as well as certain problematic, resistant bacterial strains for which there is an urgent medical need for safe and effective antimicrobial agents.

ZTI-01 (fosfomycin, FOS, for injection) demonstrates broad spectrum activity in vitro including multi-drug resistant (MDR) organisms. FOS shows no cross-resistance to other antibiotic classes and FOS mechanism of action uniquely inhibits an earlier step in peptidoglycan biosynthesis. Other antibiotic agents in combination with FOS have been proposed to enhance bacterial killing of MDR organisms. It is crucial to understand the pharmacokinetics (PK) of antimicrobials to assess the PK/pharmacodynamic parameter associated with efficacy as well as the safety, tolerability, and PK of a single dose of ZTI-01 and oral (PO) fosfomycin tromethamine in healthy subjects.

Presently, specific dosage amounts of fosfomycin have been approved for use in specific cases. Monurol® (fosfomycin tromethamine) is currently approved for uncomplicated urinary tract infections (UTIs) in women due to susceptible *Escherichia coli* and *Enterococcus faecalis* isolates and is only available as a single 3 g dose (Monurol® package insert, Forest Pharmaceuticals, Inc., 2014). Monurol® is only available as a single dose sachet for oral administration once dissolved in water and is meant for women experiencing uncomplicated UTIs.

Another approved drug, Fomicyt® (disodium fosfomycin), is only available outside of the US for intravenous administration, with dosing regimens comprising 12-24 g (12-16 g dosing for cUTI, specifically) in 2-3 divided doses (Fomicyt® package insert, Nordic Pharma UK Ltd., 2015). However, such dosing paradigm fails to take into account the development of certain increased resistance in the bacteria meant to be impacted by the drug therapy. This leads to suboptimal therapy, resulting in therapeutic failures. Similarly, the complexity of the dosing calculations for patients with renal clearance complications lead to increases in errors that negatively impact both drug efficacy and patient safety. Furthermore, it is known to be a significant problem in the art that use of equations in order to determine optimal medication dosages leads to considerable patient risks (Lesar, TS, Errors in the use of medication dosage equations, *Arch Pediatr Adolesc Med*, 152: 340-344 (1998)). While investigators have examined ways of resolving dosage errors through techniques ranging from analyses of electronic medical records (Hudali et al., Controlling antibiotics dosing errors in patients with impaired renal function using an EMR alert, UTMB Galveston (2013)) to the pairing of computerized provider order entries with clinical decision support systems (Patient Safety Network, https://psnet.ahrq.gov/primers/primer/23/medication-errors (accessed October 2017)), problems still exist within defined patient populations when it comes to developing accurate dosing regimens. Unfortunately, very recent studies have shown such problems are recognized and that an appropriate adjustment of drug doses would be highly desirable in patients with renal insufficiency, but that such dosing regimens are unavailable (Hoffmann et al., Renal insufficiency and medication in nursing home residents, *Dtsch Arztebl Int*, 113: 92-8 (2016)).

There still exists a problem in the clinical setting whereby bacterial resistance is correlated to the use of suboptimal dosing regimens. Thus there remains a need in the art to resolve problems associated with complications to disease treatment related to bacterial resistance to drug therapies by identifying proper or optimal dosing regimens commensurate with a particular disease. There also remains a need in the art to resolve problems associated with complications to disease treatment related to bacterial resistance to drug therapies by identifying proper or optimal dosing regimens commensurate with a particular patient populations and subpopulations.

SUMMARY OF THE INVENTION

The present invention provides improved dosing regimens that optimize treatment of mammals with bacterial infections using fosfomycin and are associated with enhanced efficacy over a wider MIC range, thereby encompassing bacteria that may be considered resistant and improved reductions in bacterial counts. In a related aspect, the fixed dosage adjustment improves upon the state of the art dosage schedules by simplifying and preventing calculation errors. In another aspect of the invention, the improved dosing regimens are applied to specific patient populations and subpopulations.

In one embodiment, the present invention provides a method for obtaining novel dosing regimens for fosfomycin treatment of patients with normal renal function that have improved safety and that prevent development of heteroresistant subpopulations of gram-negative and gram-positive bacteria. The methods of the present invention are also useful for providing novel dosing regimens for fosfomycin treatment of patients with impaired renal function that also improve efficacy and patient safety.

In one aspect, the present invention provides for a method of treating a patient diagnosed with a complicated UTI (cUTI), wherein the patient has an estimated creatinine clearance of >40 to ≤50 mL/min with 4 grams of fosfomycin or a pharmaceutically acceptable salt thereof intravenously every 8 hours. The duration of treatment is generally from about 3 days to about 20 days. Optionally, the duration of treatment extends from about 5 days to about 17 days, or from less than one week to more than two weeks. Alternatively, the duration of treatment lasts between 5 and 10 days. Preferably, the duration of treatment is from about 7 to about 14 days. In an alternative embodiment, the present invention provides for a dosing regimen for administering fosfomycin or a pharmaceutically acceptable salt thereof to a renally impaired patient in need of treatment wherein the renally impaired patient has an estimated creatinine clearance of >40 to ≤50 mL/min comprising administering 4 grams of fosfomycin or a pharmaceutically acceptable salt thereof intravenously every 8 hours.

In another aspect, the present invention provides for a method of treating a patient diagnosed with a cUTI and having an estimated creatinine clearance of >30 to ≤40 mL/min with, as a first dosing, 6 grams of fosfomycin or a pharmaceutically acceptable salt thereof intravenously, followed by a second dosing of 3 grams of fosfomycin or a pharmaceutically acceptable salt thereof intravenously every 8 hours. The duration of treatment is generally from about 3 days to about 20 days. Optionally, the duration of treatment extends from about 5 days to about 17 days, or from less than one week to more than two weeks. Alternatively, the duration of treatment lasts between 5 and 10 days. Preferably, the duration of treatment is from about 7 to about 14 days. An alternative embodiment of the present invention provides for a dosing regimen for administering fosfomycin or a pharmaceutically acceptable salt thereof to a renally impaired patient in need of treatment wherein the renally impaired patient has an estimated creatinine clearance of >30 to ≤40 mL/min comprising administering 6 grams of fosfomycin or a pharmaceutically acceptable salt thereof intravenously once, then with 3 grams of fosfomycin or a pharmaceutically acceptable salt thereof intravenously every 8 hours.

In a further aspect, the present invention provides for a method of treating a patient diagnosed with a cUTI and having an estimated creatinine clearance of >20 to ≤30 mL/min comprising administering to the patent 6 grams of fosfomycin or a pharmaceutically acceptable salt thereof intravenously once, followed by a second administration of 5 grams of fosfomycin or a pharmaceutically acceptable salt thereof intravenously every 24 hours. The duration of treatment is generally from about 3 days to about 20 days. Optionally, the duration of treatment extends from about 5 days to about 17 days, or from less than one week to more than two weeks. Alternatively, the duration of treatment lasts between 5 and 10 days. Preferably, the duration of treatment is from about 7 to about 14 days. In an alternative embodiment, the present invention provides for a dosing regimen for administering fosfomycin or a pharmaceutically acceptable salt thereof to a renally impaired patient in need of treatment wherein the renally impaired patient has an estimated creatinine clearance of >20 to ≤30 mL/min comprising administering a first dose of 6 grams of fosfomycin or a pharmaceutically acceptable salt thereof intravenously and a second dose of 5 grams of fosfomycin or a pharmaceutically acceptable salt thereof intravenously every 24 hours.

In a further aspect, the present invention provides for a method of treating a renally impaired patient by administering fosfomycin or a pharmaceutically acceptable salt thereof to the renally impaired patient in need of treatment wherein the renally impaired patient is diagnosed with a cUTI and has an estimated creatinine clearance of >10 to 20 mL/min, the dosing regimen comprising administering to the patent 6 grams of fosfomycin or a pharmaceutically acceptable salt thereof intravenously once, followed by a second administration of 5 grams of fosfomycin or a pharmaceutically acceptable salt thereof intravenously every 24 hours. The duration of treatment is generally from about 3 days to about 20 days. Optionally, the duration of treatment extends from about 5 days to about 17 days, or from less than one week to more than two weeks. Alternatively, the duration of treatment lasts between 5 and 10 days. Preferably, the duration of treatment is from about 7 to about 14 days. Optionally, the present invention provides for a dosing regimen for administering fosfomycin or a pharmaceutically acceptable salt thereof to a renally impaired patient in need of treatment wherein the renally impaired patient is diagnosed with a cUTI and has an estimated creatinine clearance of >10 to 20 mL/min, the dosing regimen comprising administering to the patent 6 grams of fosfomycin or a pharmaceutically acceptable salt thereof intravenously once, followed by a second administration of 5 grams of fosfomycin or a pharmaceutically acceptable salt thereof intravenously every 24 hours.

BRIEF DESCRIPTION OF THE DRAWINGS

The novel features of this invention, as well as the invention itself, both as to its structure and its operation, will be best understood from the accompanying drawings, taken in conjunction with the accompanying description, and in which:

FIG. 4 depicts demographics and baseline characteristic of the patient populations. CE=clinical evaluable; CFU=colony-forming unit; I/E=inclusion/exclusion; ITT=intent-to-treat; ME=microbiologic evaluable; MITT=modified ITT; m-MITT=microbiologic MITT; P-T=piperacillin/tazobactam; TOC=test-of-cure.

DETAILED DESCRIPTION OF THE INVENTION

Definitions

Figure 1:
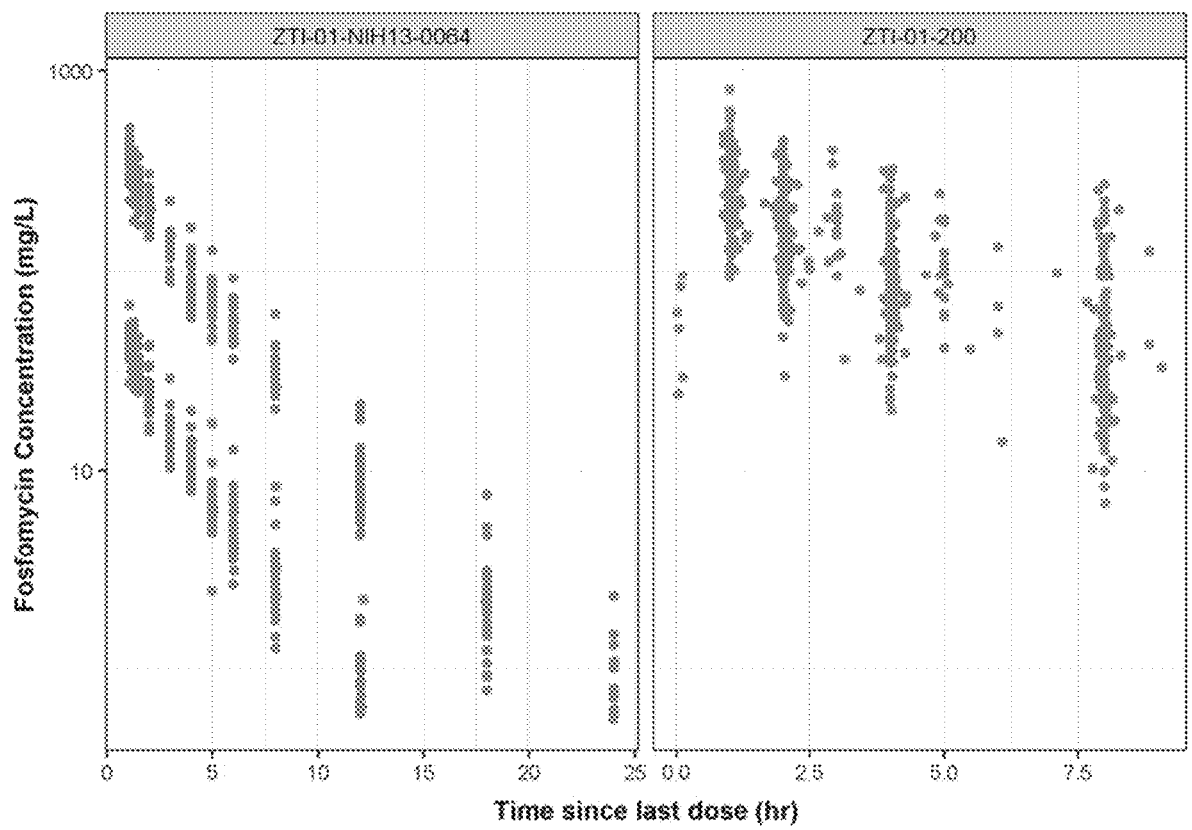
FIG. 1 shows semi-log scatterplots of fosfomycin plasma concentrations versus time, stratified by study

The term "MIC" as used herein refers to the minimum inhibitory concentration (MIC) of an antimicrobial that will inhibit the visible growth of a microorganism after overnight incubation. MICs are important in diagnostic laboratories to confirm resistance of microorganisms to an antimicrobial agent and also to monitor the activity of new antimicrobial agents. A MIC is generally regarded as the most basic laboratory measurement of the activity of an antimicrobial agent against an organism. Clinically, the MICs are used not only to determine the amount of antibiotic that a patient will receive but also the type of antibiotic used, which in turn lowers the opportunity for microbial resistance to specific antimicrobial agents. Applying MIC testing to a number of bacterial strains in the same species provides an estimate of the concentration that inhibits 50% ($MIC_{50}$) and 90% ($MIC_{90}$) of bacterial isolates and can indicate shifts in susceptibility of bacterial populations to antibiotics.

The term "RIC" as used herein refers to the resistant inhibitory concentration and identifies the concentrations of antimicrobial required to inhibit the less susceptible or 'resistant' mutant subpopulation of organisms.

The term "pharmacokinetics" (PK) as used herein refers to the time course of drug concentrations in plasma (and sometimes in other fluids and tissues) resulting from a particular dosing regimen.

The term "pharmacodynamics" (PD) as used herein expresses the relationship between drug concentrations in plasma (and sometimes in other fluids and tissues) and a resulting pharmacological effect.

A PK/PD Model combines: 1) A model describing drug concentrations vs. time (PK) with 2) A model describing the relationship of effect vs. concentration (PD), and 3) A statistical model describing variation in intra- and inter-individual PK/PD models to predict the time-course and variability of effect vs. of time.

Fosfomycin is a broad-spectrum antibiotic with broad antibacterial activity against both Gram-positive and Gram-negative pathogens, with useful activity against *E. faecalis*, *E. coli*, and various Gram-negatives like *Citrobacter* and *Proteus*.

Dose-fractionation and dose-ranging studies in a pre-clinical model system will discriminate the pharmacologic determinant of drug efficacy and thereby improve drug treatment in mammals. Moreover such studies will identify the size, shape and duration of drug exposure necessary to improve drug treatment in mammals.

The term "heteroresistance" as used herein refers to mixed populations of drug-resistant and drug-sensitive cells in a single clinical specimen or isolate where the proportion of resistant organisms may not be explicable by the natural "background" mutation rate alone; and even more precisely, heteroresistance can be defined as resistance to certain antibiotics expressed by a subset of a microbial population that is generally considered to be susceptible to these antibiotics according to traditional in-vitro susceptibility testing.

The present invention provides new methods for treating bacterial infections using fosfomycin at defined dosages based on a preferred focus on limiting the hetero-resistance of a bacterial population.

Fosfomycin is known to exert a bactericidal effect on proliferating pathogens by preventing the enzymatic synthesis of the bacterial cell wall. Fosfomycin inhibits the first stage of intracellular bacterial cell wall synthesis by blocking peptidoglycan synthesis.

The primary mechanism of resistance within bacteria is a chromosomal mutation causing an alteration of the bacterial fosfomycin transport systems. Further resistance mechanisms include enzymatic inactivation of fosfomycin by binding the molecule to glutathione (plasmid-borne resistance) or resistance acquired through cleavage of the carbon-phosphorus bond in the fosfomycin molecule (transposon-borne resistance).

While fosfomycin is generally found to be effective in-vitro against clinical isolates of certain types of bacteria, including methicillin-resistant staphylococci, vancomycin-resistant enterococci, penicillin- and erythromycin-resistant streptococci and multi-resistant *Pseudomonas*, there still exists a problem associated with resistance across cUTIs. Table 1 below lists the bacteria most commonly susceptible to fosfomycin, as well as those where resistance may be clinically problematic.

TABLE 1

Susceptibility of bacteria to fosfomycin administration

COMMONLY SUSCEPTIBLE SPECIES

Aerobic Gram-positive microorganisms
*Staphylococcus aureus*
*Streptococcus pyogenes*
*Streptococcus pneumoniae*
Aerobic Gram-negative microorganisms
*Citrobacter* spp.
*Edwardsiella* spp.
*Enterobacter cancerogenus*
*Escherichia coli*
*Haemophilus influenzae*
*Klebsiella oxytoca*
*Neisseria* spp.
*Proteus mirabilis*
*Proteus penneri*
*Providencia rettgeri*
Anaerobic microorganisms
*Peptococcus* spp.
*Peptostreptococcus* spp.
SPECIES WHERE ACQUIRED
RESISTANCE IS PROBLEMATIC Gram-positive microorganisms
*Enterococcus faecalis*
*Staphylococcus epidermidis*
Gram-negative microorganisms
*Enterobacter cloacae*
*Klebsiella pneumonia*
*Proteus inconstans*
*Pseudomonas aeruginosa*
*Serratia marcescens*
INHERENTLY RESISTANT SPECIES Gram-negative microorganisms
*Morganella morganii*
Anaerobic microorganisms
*Bacteroides* spp.

In addition to the above list, it was also observed that the dosing regimen of the present invention provided beneficial results for two uncommon and rarely treated strains. In one case, the dosing regimen of the present invention was used to administer appropriate dosages of fosfomycin, resulting in the eradication of the often resistant, Gram negative *Acinetobacter baumannii-calcoaceticus* complex. In another case, another Gram negative strain, *Raoultella ornithinolytica* was successfully eradicated while utilizing the dosing scheme of the present invention.

UTIs and, in particular, complicated UTIs occur in the urinary tract that has metabolic, functional or structural abnormalities and may involve both lower and upper tracts. It has been known that complicated UTIs significantly increase the rate of therapy failures.

The kidneys' ability to handle creatinine is known as the creatinine clearance rate, which is used to gauge the glomerular filtration rate (GFR), which is the rate of blood flow through the kidneys. The rate at which a particular substance or compound is removed from the plasma indicates kidney efficiency. This rate of removal is called renal clearance.

Tests of renal clearance can detect glomerular damage or assess the progress of renal disease. It is known that the kidneys remove creatinine, which is produced at a constant rate as a result of muscle metabolism, from the blood. While it is known that creatinine is filtered by the kidneys, it is neither reabsorbed nor secreted by the kidneys. Thus, the creatinine clearance test, which compares a patient's blood and urine creatinine concentrations, can also be used to calculate the GFR. A significant advantage is that the bloodstream normally has a constant level of creatinine. Therefore, a single measurement of plasma creatinine levels provides an index of kidney function. For example, elevated plasma creatinine levels suggest that GFR is reduced. Because nearly all of the creatinine the kidneys filter normally appears in the urine, a change in the rate of creatinine excretion may evidence a more severe renal disorder.

Compounds of the present invention include fosfomycin formulated as a pharmaceutically acceptable salt, including as a disodium salt for intravenous administration. Once inside the bacteria, fosfomycin competes with phosphoenolpyruvate to irreversibly inhibit the enzyme enolpyruvyl transferase that catalyzes the first step of peptidoglycan synthesis. Targeted patient populations include men and women, as well as pediatric or elderly subpopulations or those individuals with declining renal function.

EXAMPLES

I. Target Attainment Study:

The objective of the study was to compare the percent probabilities of PK-PD target attainment of ZTI-01 and Fomicyt® dosing regimens among simulated patients with cUTI with normal renal function and renal impairment. Patients in the PK analysis population from a previous study were replicated a sufficient number of times in order to generate a simulated patient population through use of a Gaussian distribution with a mean of 0 and added variance for differing PK parameters that contained 3,000 or more simulated fosfomycin-treated patients. This population was assessed separately six times (i.e., creating six different populations). Baseline CLcr was randomly assigned for each simulated patient using a uniform distribution from each of the following seven CLcr intervals:

>70 to 200 mL/min/1.73 m2
>50 to ≤70 mL/min/1.73 m2
>40 to ≤50 mL/min/1.73 m2
>30 to ≤40 mL/min/1.73 m2
>20 to ≤30 mL/min/1.73 m2
>10 to ≤20 mL/min/1.73 m2

With the exception of CLcr, all demographics remained the same.

Patient PK parameters were calculated for each simulated patient using demographic values and the population PK models. First, typical PK values for each simulated patient were calculated using demographic values in conjunction with the fixed effect parameter estimates for the population PK model. Individual PK parameter values for each simulated patient were then generated by applying an individual specific random effect (η) to each patient's typical PK value. Each simulated patient's η value was drawn from a Gaussian distribution with a mean of zero and a variance based on the PK parameter of interest which was estimated for the population PK model. Thus, when applied to the population of simulated patients, each cohort of simulated patients with the same demographics in the simulated population had individually generated PK parameters, resulting in distinct simulated patients.

A. Generation of Fosfomycin Exposures for Simulated Patients

Using the final population PK model based on the study and the individual PK parameters generated as described previously, total-drug concentration-time profiles were generated for each simulated patient after administration of three dosing regimens based upon their CLcr (in units of mL/min/1.73 m2) as specified in Table 2. Individual total-drug plasma concentration-time profiles were generated for each simulated patient from 0 to 48 hours after administration of the dosing regimens. Total drug plasma AUC values were then calculated by numerical integration of the concentration-time profiles. Total-drug AUC:MIC ratios were calculated by dividing average total-drug plasma AUC from 0 to 24 hours (which represented the AUC from 0 to 48 hours divided by 2) by fixed MIC values ranging from 0.5 to 256 mg/L. Total-drug plasma fosfomycin % T>RIC was determined for each patient by counting the total number of total-drug concentrations that were above a given MC value, multiplying this number by the time interval between simulated concentrations (0.1 hour), and then dividing this product by 48 hours.

TABLE 2

ZTI-01 and Fomicyt® dosing recommendations for simulated cUTI patients by renal function group

| CLcr range for each renal function group (mL/min/1.73 m$^2$) | ZTI-01 dosing recommendations | Fomicyt® dosing recommendations[a] | |
|---|---|---|---|
| | | 12 g | 16 g |
| >50 | 6 g q8 h | 4 g q8 h | 8 g q 12 h |
| >40 to 50 | 4 g q8 h | 4 g loading followed by 2.8 g q8 h | 8 g loading followed by 5.6 g q 12 h |
| >30 to 40 | 6 g loading dose followed by 3 g q8 h | 4 g loading followed by 2.4 g q8 h | 8 g loading followed by 4.8 g q 12 h |
| >20 to 30 | 6 g loading dose followed by 5 g q24 h | 4 g loading followed by 1.6 g q8 h | 8 g loading followed by 3.2 g q 12 h |
| >10 to 20 | 6 g loading dose followed by 5 g q24 h | 4 g loading followed by 2.4 g q24 h | 8 g loading followed by 3.2 g q24 h |

[a]The first dose should be increased by 100% (loading dose), but must not exceed 8 g (Fomicyt® package insert, Nordic Pharma, June 2015)

B. Non-Clinical Pharmacokinetic-Pharmacodynamic Targets for Efficacy

Total-drug plasma ratio of the area under the concentration-time curve (AUC) to the minimum inhibitory concentration (MIC) (AUC:MIC ratio) and the percentage of total-drug concentrations that were above resistance inhibitory concentration (% T>RIC) targets for net bacterial stasis and a 1-log 10 CFU reduction from baseline for Enterobacteriaceae, as shown in Table 3, were evaluated. Emphasis was placed on the assessment of PK-PD target attainment results for AUC:MIC ratio and % T>RIC targets associated with net bacterial stasis.

TABLE 3

Summary of total-drug AUC:MIC ratio targets and % T > RIC targets for fosfomycin against *Enterobacteriaceae*

| Endpoint | Total-drug AUC:MIC ratio | Total-drug % T > RIC |
|---|---|---|
| Net bacterial stasis | 19.1 | 11.9 |
| 1-log₁₀ CFU reduction from baseline | 41.6 | 20.9 |
| 2-log₁₀ CFU reduction from baseline | — | 32.8 |

C. Percent Probabilities of PK-PD Target Attainment by MIC

Summary of percent probabilities of PK-PD target attainment by MIC or RIC based on the assessment of total-drug AUC:MIC ratio or % T>RIC targets for Enterobacteriaceae efficacy among simulated patients with cUTI by CLcr group after administration of ZTI-01 and Fomicyt® dosing regimens are shown in Table 4.

TABLE 4

Summary of percent probabilities of PK-PD target attainment by MIC or RIC, based on the assessment of total-drug AUG:MIC ratio targets and % T > RIC against Enterobacteriaceae, among simulated patients by CLcr group after administration of for ZTI-01 and Fomicyt ® dosing regimens

| PK-PD target for net bacterial stasis | CLcr mL/min/ 1.73 m² groups | Percent probabilities of PK-PD target attainment by MIC (mg/L) or RIC[a] | | | | | | | | | | | |
|---|---|---|---|---|---|---|---|---|---|---|---|---|---|
| | | ZTI-01 | | | | Fomicyt ® 12 g | | | | Fomicyt ® 16 g | | | |
| | | 16 | 32 | 64 | 128 | 16 | 32 | 64 | 128 | 16 | 32 | 64 | 128 |
| AUC:MIC ratio | >10 to ≤20 | 100 | 100 | 93.8 | 51.8 | 100 | 97.3 | 65.8 | 14.9 | 100 | 100 | 95.2 | 55.9 |
| | >20 to ≤30 | 100 | 99.5 | 86.9 | 38.3 | 100 | 99.6 | 87.9 | 38.2 | 100 | 100 | 97.9 | 72.4 |
| | >30 to ≤40 | 100 | 100 | 97.0 | 64.2 | 100 | 99.8 | 89.4 | 41.4 | 100 | 100 | 97.9 | 70.4 |
| | >40 to ≤50 | 100 | 100 | 95.0 | 56.0 | 100 | 99.6 | 84.4 | 34.3 | 100 | 100 | 95.8 | 61.4 |
| | >50 to ≤70 | 100 | 100 | 97.2 | 66.7 | 100 | 99.3 | 84.3 | 35.0 | 100 | 99.9 | 95.0 | 59.7 |
| | >70 | 100 | 99.1 | 82.0 | 32.1 | 99.9 | 93.1 | 54.4 | 10.6 | 100 | 98.2 | 75.2 | 26.0 |
| % T > RIC | >10 to ≤20 | 100 | 100 | 99.7 | 75.2 | 100 | 100 | 86.3 | 26.0 | 100 | 100 | 99.6 | 77.6 |
| | >20 to ≤30 | 100 | 99.9 | 98.6 | 66.2 | 100 | 100 | 94.0 | 43.2 | 100 | 100 | 99.9 | 86.2 |
| | >30 to ≤40 | 100 | 100 | 99.7 | 80.1 | 100 | 100 | 97.6 | 56.1 | 100 | 100 | 99.9 | 92.1 |
| | >40 to ≤50 | 100 | 100 | 99.7 | 80.8 | 100 | 100 | 97.4 | 54.0 | 100 | 100 | 99.9 | 91.1 |
| | >50 to ≤70 | 100 | 100 | 100 | 93.1 | 100 | 100 | 98.7 | 67.1 | 100 | 100 | 100 | 93.6 |
| | >70 | 100 | 100 | 99.5 | 79.4 | 100 | 100 | 94.1 | 39.9 | 100 | 100 | 99.2 | 78.5 |

Note:
Shaded cells indicate percent probabilities of PK-PD target attainment by MIC or RIC ≥90%.
[a]RIC represents the MIC without G6P, which was six fold higher than the MIC.

At a MIC value of 32 µg/mL, percent probabilities of attaining the total-drug plasma AUC:MIC ratio target associated with net bacterial stasis ranged from 99.1 to 100% across CLcr groups for simulated patients after administration of ZTI-01 dosing regimens. For the Fomicyt® 12 and 16 dosing regimens, percent probabilities at this MIC value ranged from 93.1 to 99.8 and 98.2 to 100%, respectively, across CLcr groups for simulated patients. At a MIC value of 64 µg/mL, percent probabilities of attaining the total-drug plasma AUC:MIC ratio target associated with net bacterial stasis ranged from 82.0 to 97.2% across CLcr groups for simulated patients after administration of ZTI-01 dosing regimens. For the Fomicyt® 12 and 16 dosing regimens, percent probabilities at this MIC value ranged from 54.4 to 89.4% and 75.2 to 97.9%, respectively, across CLcr groups for simulated patients.

At a RIC value of 32 µg/mL, percent probabilities of attaining the total-drug % T>RIC ratio target associated with net bacterial stasis ranged from 99.9 to 100%, respectively, across CLcr groups for simulated patients after administration of ZTI-01 dosing regimens. For the Fomicyt® 12 and 16 dosing regimens, percent probabilities at this RIC value were 100% across CLcr groups. At a RIC value of 64 µg/mL, percent probabilities of attaining the total-drug % T>RIC ratio target associated with net bacterial stasis ranged from 98.6 to 100% across CLcr groups for simulated patients after administration of ZTI-01 dosing regimens. For Fomicyt® 12 and 16 dosing regimens, percent probabilities at this RIC value ranged from 86.3 to 98.7% and 99.2 to 100%, respectively, across CLcr groups for simulated patients. The unique dosing regimen of ZTI-01 results in superior and unexpected benefits to patients without the need to rely on the problematic dosing calculations of the prior art. 6 g. ZTI-01, administered 3 times a day, would reduce the safety concerns and improve efficacy across the target patient population.

II. Population Pharmacokinetic Analysis of ZTI-01 Using Data from Healthy Subjects and Patients with Complicated Urinary Tract Infections Methods: Two clinical studies have been conducted as part of the development of ZTI-01: a Phase 1 study in healthy subjects (ZTI-01-NIH13-0064) and a Phase 2/3 study in hospitalized patients with complicated urinary tract infections (ZTI-01-200). A PPK model, originally developed using Phase 1 data and an empirical relationship between FOS clearance (CLt) and creatinine clearance (CLcr) [Microbe 2017 Abstr. P1134], was refined using pooled data from healthy subjects and patients with cUTI, including acute pyelonephritis.

The PPK model was developed in NONMEM 7.2. In the Phase 1 study, 28 healthy subjects who received ZTI-01 as single (1 and 8 g infused over 1 hour) IV doses in crossover fashion provided plasma and urine samples for FOS concentration determination over 24 hours. Patients from the Phase 2/3 study (ZEUS, NCT02753946.) received ZTI-01 at 6 g every 8 hours, with dosage adjustment for patients with renal impairment (adjusted for CLcr≤50 mL/min). Blood samples for PK (n=5 per patient) were collected on Day 1 and on either Days 3, 4, or 5. Model development involved refinement of the previous CLt:CLcr relationship using the pooled data and a full covariate analysis to identify other patient descriptors associated with the interindividual variability (IIV) in FOS PK. Model qualification included standard goodness-of-fit metrics and visual predictive check plots.

For the PPK model refinement, previous structural population PK model was fit to the pooled Phase 1 and 2/3 data. Covariate analyses were conducted using forward selection and backward elimination. The final model was qualified using visual predictive checks and non-parametric bootstrap procedures. Individual, post-hoc fosfomycin exposures were calculated for each patient using predicted plasma fosfomycin concentration-time data for the first 48 hours of therapy.

Results: A total of 1408 plasma concentrations from 242 subjects/patients were analyzed, with 310 urine samples from the 28 Phase 1 subjects (FIG. 1). The demographics of the subjects included in the two studies are described below in Table 5.

TABLE 5

Summary statistics or counts of the subject demographic characteristics of analysis population

| Variable | Study ZTI-01-13-0064 (N = 28) | Study ZTI-01-200 (N = 224) | Pooled N = 252 |
|---|---|---|---|
| Age (yr) | 25.5 (18-37) | 54 (18-89) | 36 (18-89) |
| BMI (kg/m$^2$) | 24 (20.6-29.8) | 25.2 (15.8-48.9) | 24.7 (15.8-48.9) |
| BSA (m$^2$) | 1.75 (1.59-2.13) | 1.82 (1.4-2.33) | 1.80 (1.40-2.33) |
| Height (cm) | 168 (152-188) | 166 (147-194) | 166 (147-194) |
| CLcm (mL/min/1.73 m$^2$) | 132 (92.8-186) | 82.2 (17.4-224) | 97.8 (17.4-224) |
| Weight (kg) | 69.1 (55.0-94.4) | 72.1 (43.1-117) | 70.7 (43.1-117) |
| Gender | | | |
| Male | 12/28 (42.9%) | 81/224 (36.2%) | 93/252 (36.9%) |
| Female | 16/28 (57.1%) | 143/224 (63.8%) | 159/252 (63.1%) |
| Race | | | |
| White | 21/28 (75%) | 224/224 (100%) | 245/252 (97.2%) |
| Black | 7/28 (25%) | 0/224 (0.00%) | 7/252 (2.78%) |
| Infection Type | | | |
| Healthy | 28/28 (100%) | 0/224 (0.00%) | 28/252 (11.1%) |
| AP | 0/28 (0.00%) | 115/224 (51.3%) | 115/252 (45.6%) |
| CUTI | 0/28 (0.00%) | 109/224 (48.7%) | 109/252 (43.3%) |

Note:
Continuous variables are reported as median (range); categorical variables as n/N (%).

Figure 2:
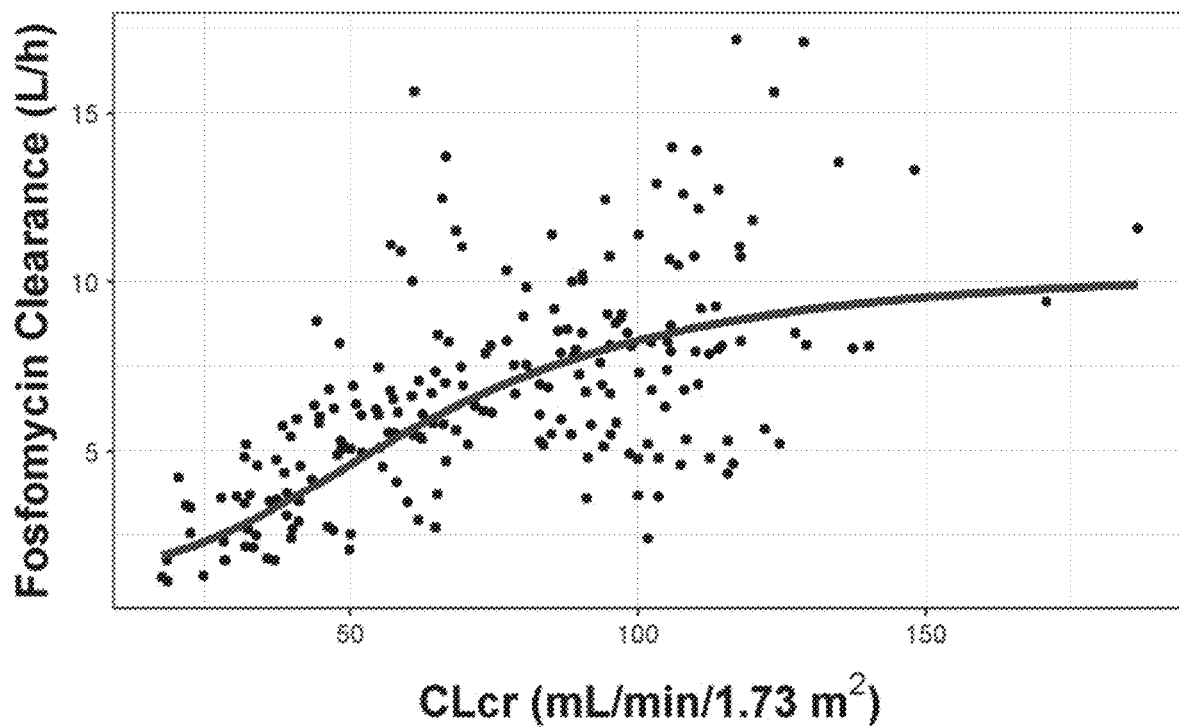
FIG. 2 depicts the relationship between fosfomycin clearance and CLcr.

The most robust fit to pooled Phase 1 and 2/3 studies was obtained using the three compartment model with a zero-order rate constant for the IV infusion and first-order elimination. The only clinically relevant, covariate relationship was between CLR and Clcr, which was modeled using a sigmoidal Hill-type function (FIG. 2).

Additional statistically-significant covariate relationships include:

Weight and CL; BSA and Vc; infection type and CLd1; and BSA and infection type and Vp1.

Evaluations of the normalized prediction distribution errors, bootstrap PK parameter estimates, and prediction-corrected visual predictive check plots indicate that the model is providing a precise and unbiased fit to the data and that model-based simulations adequately capture the observations. Summary statistics of the bootstrap PK parameters are further described at Table 6.

TABLE 6

Summary statistics of the bootstrap PK parameters in comparison to the final population PK model parameter estimates and associated standard errors

| | Final Model | | Bootstrap Statistics (N = 200) | | | |
|---|---|---|---|---|---|---|
| Parameter | Find estimate | % SEM | Mean | Median | % CV | 90% CI |
| CL (L/hr) | | | | | | |
| Non-renal CL (L/hr) | 1.61 | 12 | 1.62 | 1.63 | 12.9 | 1.27-1.98 |
| $CL_R$ maximum (L/hr) | 8.87 | 8.01 | 9.02 | 8.87 | 8.7 | 7.86-10.3 |
| Baseline $CLcr_{50}$ (mL/min/1.73 m$^2$) | 65 | 8.6 | 66.3 | 65.6 | 8.82 | 57.9-76.2 |
| Hill coefficient | 2.56 | 12.8 | 2.6 | 2.59 | 13.5 | 2.03-3.29 |
| CL-weight power | 0.741 | 14.5 | 0.741 | 0.745 | 13.9 | 0.568-0.894 |
| Vc (L) | | | | | | |
| Coefficient | 17.6 | 5.13 | 17.7 | 17.7 | 4.74 | 16.1-18.9 |
| Vc-BSA power | 1.76 | 16.9 | 1.72 | 1.7 | 17.9 | 1.23-2.16 |
| CLd1 (L/hr) | | | | | | |
| Coefficient | 4.15 | 30.9 | 4.36 | 4.2 | 29.1 | 2.64-6.61 |
| Proportional increase for AP and cUTI patients | 1.24 | 45.9 | 1.28 | 1.15 | 51.3 | 0.43-2.56 |
| Vp1 (L) | | | | | | |
| Coefficient | 5.99 | 16.7 | 6.11 | 6.03 | 15 | 4.61-7.69 |
| Vp1-BSA power | 2.72 | 23.3 | 2.73 | 2.73 | 24.1 | 1.73-3.72 |
| Proportional increase for AP and cUTI patients | 0.729 | 43.2 | 0.721 | 0.706 | 43 | 0.293-1.26 |
| CLd2 (L/hr) | | | | | | |
| Coefficient | 0.349 | 17.8 | 0.351 | 0.346 | 14.7 | 0.273-0.441 |
| Vp2 (L) | | | | | | |
| Coefficient | 1.73 | 13.5 | 1.74 | 1.72 | 11.2 | 1.44-2.06 |
| $\omega^2$ for CL | 0.111 | 10.9 | 0.108 | 0.108 | 12.6 | 0.0851-0.128 |
| $\omega^2$ for Vc | 0.175 | 25.1 | 0.174 | 0.172 | 23.7 | 0.11-0.243 |
| $\omega^2$ for CLd1 | 0.215 | 33.9 | 0.203 | 0.199 | 46.1 | 0.0648-0.355 |
| $\omega^2$ for Vp1 | 0.502 | 21.1 | 0.516 | 0.508 | 24.1 | 0.324-0.722 |
| IOV on CL | 0.00517 | 20.5 | 0.00515 | 0.00502 | 22 | 0.00329-0.00696 |
| Covariance between CL and Vc | 0.0721285 | 22 | 0.0707 | 0.0704 | 23.6 | 0.0475-0.0977 |
| Covariance between CL and Vp1 | 0.12962 | 22.2 | 0.134 | 0.131 | 24.1 | 0.0844-0.194 |
| Covariance between CLd1 and Vp1 | 0.185328 | 52.4 | 0.173 | 0.166 | 56.8 | 0.00699-0.334 |
| Plasma Residual variability ($\sigma^2$) | | | | | | |
| CCV component | 0.0195 | 11.7 | 0.0196 | 0.0194 | 11.2 | 0.0163-0.0232 |
| Urine Residual variability ($\sigma^2$) | | | | | | |
| Additive component | 1.05 | 54.2 | 1.01 | 0.852 | 129 | 0.124-2.17 |
| CCV component | 0.0795 | 13.1 | 0.0793 | 0.079 | 13.1 | 0.0623-0.0973 |

TABLE 7

Summary (geometric mean [% CV]) of key fosfomycin PK parameters in infected patients from ZTI-01-200 receiving doses selected based upon the patient's baseline renal function, derived from the fit of the population PK model

| Parameter | Phase 2/3 Patients (n = 214) |
|---|---|
| $AUC_{0-24}$ (mg · h/L)$^a$ | 2490 (36.8) |
| CL (L/h) | 5.98 (51.9) |
| $C_{max}$ (mg/L)$^b$ | 364 (36.7) |
| $C_{min}$ (mg/L)$^c$ | 30.0 (62.7) |
| $t_{1/2, \alpha}$ (h) | 0.402 (37.0) |
| $t_{1/2, \beta}$ (h) | 2.67 (20.4) |
| $t_{1/2, \gamma}$ (h) | 4.99 (30.5) |
| $V_{SS}$ (L) | 30.9 (38.7) |

Conclusions: A three-compartment model with zero-order IV input and first-order elimination best characterized the time-course of fosfomycin in healthy subjects and infected patients. Based on the evaluation of the post-hoc fosfomycin $AUC_{0-24}$, $C_{max}$ and $C_{min}$, none of the covariate effects other than CLcr were found to impact fosfomycin exposure to a significant extent. The final population PK model for fosfomycin was considered reliable for conducting simulations and for generating individual post-hoc estimates of exposure for use in subsequent PK-PD analyses for safety and efficacy.

III. Intravenous Fosfomycin (ZTI-01) for the Treatment of Complicated Urinary Tract Infections (cUTI) Including Acute Pyelonephritis (AP): Results from a Multi-Center, Randomized, Double-Blind Phase 2/3 Study in Hospitalized Adults (ZEUS)

Figure 3:
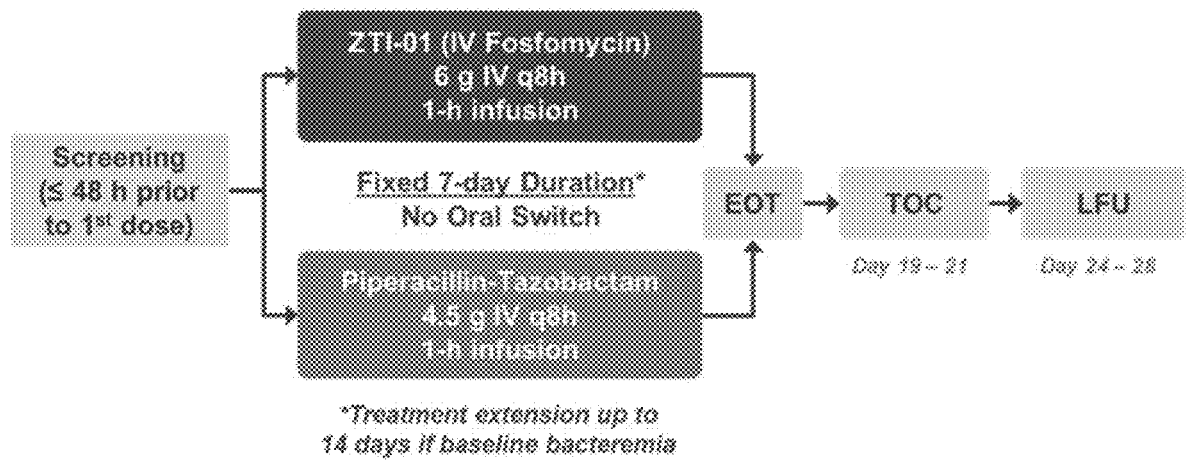
FIG. 3 shows the study design to evaluate safety and efficacy of ZTI-01 in hospitalized adults. EOT=end-of-treatment; LFU=late follow-up visit; TOC=test of cure.

Methods: ZEUS study was a multicenter, randomized, double-blind Phase 2/3, noninferiority trial designed to evaluate safety and efficacy of ZTI-01 in hospitalized adults with cUTI or AP versus P-T (FIG. 3). The primary endpoint of overall success was defined as clinical cure plus microbiologic eradication in the microbiologic modified intent-to-treat (m MITT) population at the test-of-cure (TOC) visit (Day 19).

Sample size of 230 patients per arm (N=460), was based on 15% NI margin, 70% predicted evaluability rate, 70% overall success rate in both treatment groups, 80% power, 1-sided α=0.025. Patients were randomized (n=465) and treated (n=464) to receive 6 g ZTI-01 as a one-hour IV infusion q8 h (18 g total daily dose) or 4.5 g IV P-T as a one-hour infusion q8 h (13.5 g total daily dose) for a fixed 7 days, except patients with concurrent bacteremia with option to receive up to 14 days. Oral step-down therapy was prohibited (FIG. 4).

A post-hoc analysis using pulsed-field gel electrophoresis (PFGE) was performed to molecularly type all baseline and TOC pathogens (both treatment arms), in order to confirm microbiological eradication/persistence; a total of 20 post-baseline pathogens were identified as unique, unrelated strains compared to baseline.

Results: Patients were well matched in the ZTI-01 and P-T populations, with slightly more patients being diagnosed with acute pyelonephritis than cUTI. Table 8 describes the patient demographics.

which was only 44% effective at a dosing regimen of 8 g bid. While both studies examined patients having reduced renal clearance, the significant improvement of therapeutic effectiveness based on dosing regimen (6 g tid versus 8 g bid) highlights the importance of resolving known problems associated with complications to disease treatment related to bacterial resistance to drug therapies by identifying proper or optimal dosing regimens commensurate with a particular patient populations and subpopulations.

Figure 5:
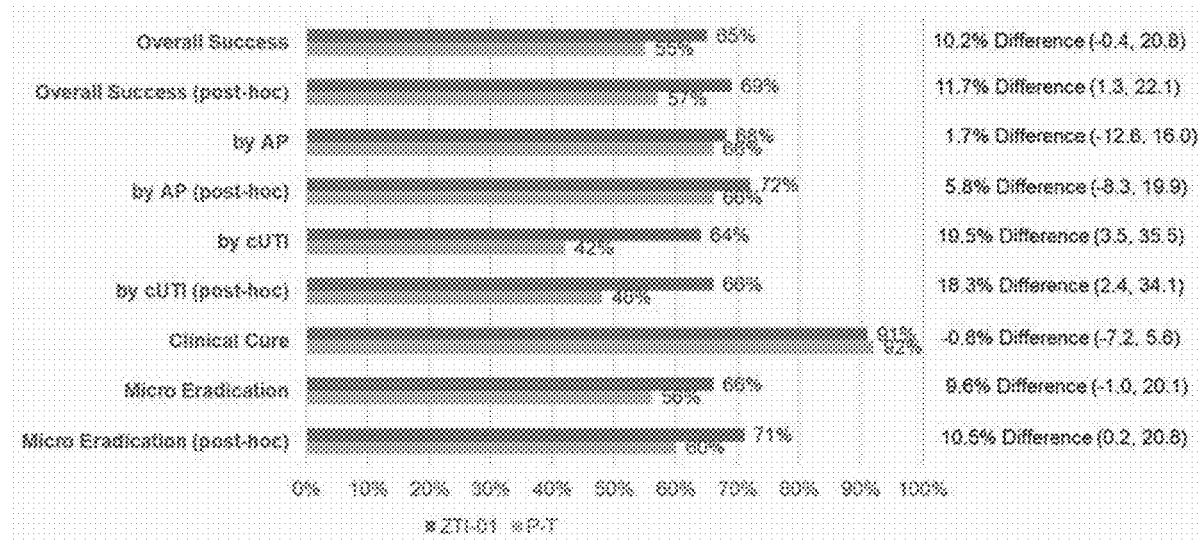
FIG. 5 shows overall response, overall response by baseline diagnosis, clinical cure and microbiologic eradication at TOC (m-MITT). Treatment difference=difference in overall success rate between two treatment arms (the 95% CI (2-sided) is computed using a continuity-corrected Z-statistic); overall success=clinical outcome of cure or improvement and microbiologic outcome of eradication (defined as the baseline bacterial pathogen being reduced to ≤$10^4$ CFU/ml); TOC=test of cure; m-MTT=microbiologic modified intent to treat population. Post-hoc analysis: PFGE was performed to molecularly type all baseline and TOC pathogens (both treatment arms) in order to confirm microbiological eradication/persistence. A total of 20 post-baseline pathogens were identified as unique, unrelated strains compared to baseline.

Clinical cure rates at TOC were high and similar between treatment groups (>90%) (FIG. 5). Table 9 displays the clinical response at TOC, by population analysis.

TABLE 9

Clinical Response at TOC, by Analysis Populations

| Population | | ZTI-01 n (%) | P-T n (%) | Treatment Difference (95% CI) |
|---|---|---|---|---|
| MITT | N1 | 233 | 231 | |
| | Cure | 211 (90.6%) | 212 (91.8%) | −1.2% |
| | Failure | 11 (4.7%) | 16 (6.9%) | (−6.8, 4.4) |
| | Indeterminate | 11 (4.7%) | 3 (1.3%) | |
| m-MITT | N1 | 184 | 178 | |
| | Cure | 167 (90.8%) | 163 (91.6%) | −0.8% |
| | Failure | 9 (4.9%) | 12 (6.7%) | (−7.2, 5.6) |
| | Indeterminate | 8 (4.3%) | 3 (1.7%) | |

TABLE 8

Patient Demographics: Primary Analysis Population (m-MITT)

| | ZTI-02 N = 184 | P-T N = 178 | TOTAL N = 362 |
|---|---|---|---|
| Primary Diagnosis | | | |
| AP | 99 (53.8%) | 94 (52.8%) | 193 (53%) |
| cUTI | 85 (46.2%) | 84 (47.2%) | 169 (47%) |
| Age > 65 yrs | 62 (33.7%) | 63 (35.4%) | 125 (34.5%) |
| Gender, n (%), Female:Male | 119 (64.7%):65 (35.3%) | 111 (62.4%):67 (37.6%) | 230 (63.5%):132 (36.5%) |
| Race, n (%) White | 184 (100%) | 178 (100%) | 362 (100%) |
| Mean BMI, kg/m$^2$ (SD), (Min-Max Range) | 25.75 (5.26) 17.1-48.9 | 26.64 (5.84) 15.6-44.6 | 26.18 (5.56) 15.6-48.9 |
| CrCl, ≥ 20-50 mL/min | 26 (14.1%) | 20 (11.2%) | 46 (12.7%) |
| SIRS at Baseline | 62 (33.7%) | 52 (29.2%) | 114 (31.5%) |
| Bacteremia at Baseline | 19 (10.3%) | 13 (7.3%) | 32 (8.3%) |
| No prior short acting antibiotics | 168 (91.3%) | 169 (94.9%) | 34 (93.0%) |

AP = acute pyelonephritis; BMI = body mass index; CrCl = creatinine clearance; cUTI = complicated urinary tract infection; SIRS = systemic inflammatory response syndrome.

ZTI-01 met the primary endpoint of non-inferiority to P-T in overall success at TOC in the m-MITT population; overall success rates were of 64.7% vs. 54.5%, respectively (difference 10.2%, 95% CI: −0.4, 20.8) (FIG. 5).

Using unique pathogens strains typed by PFGE, overall success rates were 69.0% for ZTI-01 vs 57.3% for P-T (difference 11.7% 95% CI: 1.3, 22.1). The overall success rates for patients with AP were similar between treatment groups, and numerically favored ZTI-01 patients with cUTI (FIG. 5). Earlier studies have examined fosfomycin dosing against similar pathogens for patients with AP (Ode, B. et al., Fosfomycin Versus Ampicillin in the Treatment of Acute Pyelonephritis, *Chemioterapia*, 7(2): 96-100 (1988)). Surprisingly, ZTI-01 was 68% effective at the preferred dosing regimen (6 g tid) when compared with the Ode et al. study, TABLE 9-continued Clinical Response at TOC, by Analysis Populations

| Population | | ZTI-01 n (%) | P-T n (%) | Treatment Difference (95% CI) |
|---|---|---|---|---|
| CE-TOC | N1 | 199 | 196 | 1.6% |
| | Cure | 188 (94.5%) | 182 (92.9%) | (−3.7, 6.9) |
| | Failure | 11 (5.5%) | 14 (7.1%) | |

TABLE 9-continued

Clinical Response at TOC, by Analysis Populations

| Population | | ZTI-01 n (%) | P-T n (%) | Treatment Difference (95% CI) |
|---|---|---|---|---|
| ME-TOC | N1 | 155 | 145 | 2.4% |
| | Cure | 148 (95.5%) | 135 (93.1%) | (−3.5, 8.3) |
| | Failure | 7 (4.5%) | 10 (6.9%) | |

N1 - percentages are calculated using N1, the number of patients in the corresponding analysis population;
Persistence: ≥ 10⁴ CFU/mL; Persistence + Indeterminate = Failure
CE = clinical evaluable;
ME = microbiologic evaluable;
MITT = modified intent-to-treat;
m-MITT = microbiologic MITT;
P-T = piperacillin/tazobactam;
TOC = test-of-cure Microbiological response rates were higher in the ZTI-01 arm vs the P-T arm (FIG. 5). Table 10 describes the microbiological response at TOC.

TABLE 10

Microbiological Response, at TOC by Analysis Populations

| Population | | ZTI-01 n (%) | P-T n (%) |
|---|---|---|---|
| Original Analysis | | | |
| m-MITT | N1 | 184 | 178 |
| | Eradication | 121 (65.8%) | 100 (56.2%) |
| | Persistence | 50 (27.2%) | 69 (38.8%) |
| | Indeterminate | 13 (7.1%) | 9 (5.1%) |
| ME-TOC | N1 | 155 | 145 |
| | Eradication | 109 (70.3%) | 86 (59.3%) |
| | Persistence | 46 (29.7%) | 59 (40.7%) |
| Post-hoc Analysis Using PFGE Typing* | | | |
| m-MITT | N1 | 184 | 178 |
| | Eradication | 130 (70.7%) | 107 (60.1%) |
| | Persistence | 41 (22.3%) | 62 (34.8%) |
| | Indeterminate | 13 (7.1%) | 9 (5.1%) |
| ME-TOC | N1 | 155 | 145 |
| | Eradication | 117 (75.5%) | 93 (64.1%) |
| | Persistence | 38 (24.5%) | 52 (35.9%) |

N1 - percentages are calculated using N1, the number of patients in the corresponding analysis population;
Persistence: ≥ 10⁴ CFU/mL; Persistence + Indeterminate = Failure;
Post-hoc analysis: PFGE was performed to molecularly type all baseline and TOC pathogens (both treatment arms), in order to confirm microbiological eradication/persistence; a total of 20 post-baseline pathogens were identified as unique, unrelated strains compared to baseline Microbiological response rates at TOC varied among patients with severe disease (i.e., sepsis (based on SIRS criteria) or bacteremia); however, clinical cure rates in these subgroups were similar between treatment groups. Table 11 shows overall clinical/microbiological response at TOC across certain populations.

TABLE 11

Overall, Clinical and Microbiological Responses at TOC in Bacteremia and SIRS Populations (m-MITT)

| Population | | ZTI-01 n (%) | P-T n (%) |
|---|---|---|---|
| Bacteremia | | | |
| Overall Response | N1 | 19 | 13 |
| | Eradication | 9 (47.4%) | 5 (38.5%) |
| | Persistence | 7 (36.8%) | 8 (61.5%) |
| | Indeterminate | 3 (15.8%) | 0 (0%) |
| Clinical Response | N1 | 19 | 13 |
| | Eradication | 15 (78.9%) | 10 (76.9%) |
| | Persistence | 2 (10.5%) | 3 (23.1%) |
| | Indeterminate | 2 (10.5%) | 0 (0%) |
| Per-patient Microbiological Response | N1 | 19 | 13 |
| | Eradication | 9 (47.4%) | 6 (46.2%) |
| | Persistence | 6 (31.6%) | 7 (53.8%) |
| | Indeterminate | 4 (21.2%) | 0 (0%) |
| SIRS | | | |
| Overall Response | N1 | 62 | 52 |
| | Eradication | 41 (66.1%) | 39 (75.0%) |
| | Persistence | 16 (25.8%) | 11 (21.2%) |
| | Indeterminate | 5 (8.1%) | 2 (3.8%) |
| Clinical Response | N1 | 62 | 52 |
| | Eradication | 55 (88.7%) | 48 (92.3%) |
| | Persistence | 3 (4.8%) | 2 (3.8%) |
| | Indeterminate | 4 (6.5%) | 2 (3.8%) |
| Patient Microbiological Response | N1 | 62 | 52 |
| | Eradication | 41 (66.1%) | 40 (76.9%) |
| | Persistence | 14 (22.6%) | 10 (19.2%) |
| | Indeterminate | 7 (11.3%) | 2 (3.8%) |

ZTI-01 was generally well tolerated and the majority of adverse effects (AEs) were mild to moderate. In the safety population (n=464), treatment-emergent adverse events (TEAEs) were observed in 42.1% and 32.0% of patients in the ZTI-01 and P-T groups, respectively. Table 12 provides an overview of all AEs within the MITT safety population.

TABLE 12

Overview of AEs (MITT Safety Population)

| n (%) | ZTI-01 (n = 233) | P-T (n = 231) |
|---|---|---|
| Any AEs | 99 (42.5%) | 74 (32.0%) |
| Any TEAEs | 98 (42.1%) | 74 (32.0%) |
| Mild | 84 (36.1%) | 49 (21.2%) |
| Moderate | 35 (15.0%) | 38 (16.5%) |
| Severe | 5 (2.1%) | 4 (1.7%) |
| Drug-related TEAEs | 48 (20.6%) | 32 (13.9%) |
| SAEs | 5 (2.1%) | 6 (2.6%) |
| Drug-related SAE | 1 (0.4%) | 1 (0.4%) |
| TEAEs leading to study drug discontinuation | 7 (3.0%) | 6 (2.6%) |
| Serious TEAEs leading to study drug discontinuation | 0 (0%) | 1 (0.4%) |

Most TEAEs were mild-to-moderate in severity; premature discontinuation of study drug was uncommon. The most common TEAEs were asymptomatic, reversible laboratory abnormalities (e.g., elevated ALT/AST and hypokalemia). The most frequent clinical TEAEs were transient GI events (e.g., nausea, vomiting).

Severe TEAEs and serious adverse events (SAEs) were uncommon (Table 12); 1 SAE was related to study drug in each treatment group (ZTI-01: hypokalemia; P-T: renal insufficiency). No deaths reported during the study.

Conclusion: ZTI-01 was superior to P-T in overall success among patients with cUTI and AP. Among treatment arms, cure rates were high and microbiologic eradication rates favored ZTI-01. ZTI-01 was well-tolerated, with the most common types of AEs (asymptomatic laboratory abnormalities and transient GI events) being consistent with class effects described over the past >45 years of use outside the U.S.

IV. Pharmacokinetics-Pharmacodynamics Target Attainment Analyses to Support ZTI-01 (Fosfomycin for Injection) Dose Selection for Patients with Complicated Urinary Tract Infections (cUTI)

ZTI-01, fosfomycin for injection, has in vitro activity against Gram-positive and -negative organisms, including carbapenem-resistant Enterobacteriaceae. ZTI-01 is currently in Phase 2/3 development for the treatment of patients with complicated urinary tract infections (cUTI). Pharmacometric analyses which integrate non-clinical pharmacokinetic-pharmacodynamic (PK-PD) targets for efficacy, population pharmacokinetics (PK), and in vitro surveillance data provide the opportunity to evaluate dosing regimens considered for clinical studies. PK-PD target attainment analyses were undertaken to provide support for ZTI-01 dosing recommendations to treat patients with cUTI.

Methods:

Simulated Patient Populations

Monte Carlo simulation was carried out in R 3.1.2 to generate a population of 6,000 patients with varying creatinine clearance (CLcr). Parameter estimates from a previously developed population PK model were used to generate total-drug plasma concentration-time profiles: The population PK model demonstrated that a three-compartment model with zero-order input and first-order elimination best described the PK data in healthy Phase 1 subjects. For the purpose of extrapolating exposures in patient populations, the population PK model was revised to incorporate allometric scaling and an empiric relationship between CLr and CLcr (Trang et al. Population pharmacokinetic analysis of ZTI-01 (Fosfomycin for Injection) using Phase 1 data for ZTI-01 and evaluation of a Phase 2/3 sparse PK sampling strategy. *American Society of Microbiology Microbe* 2017, New Orleans, La., Jun. 1-5, 2017).

CLcr values were generated using a uniform probability distribution for the following renal function groups (1,000 each): 70-150, 50-70, 40-50, 30-40, 20-30, and 10-20 mL/min/1.73 m2. Weight was generated by randomly sampling with replacement from a clinical database of infected patients.

Generation of Fosfomycin Exposures for Simulated Patients

Using the demographics for simulated patients and parameter estimates and a variance-covariance matrix based on the population PK model, key PK parameter estimates were calculated for each simulated patient.

Using the population PK model and the individual PK parameters generated, total-drug concentration-time profiles were generated from 0 to 24 hours on Day 1 for each simulated patient by assigning a dosing regimen based upon their CLcr as specified by Table 13.

TABLE 13

Summary of ZTI-01 Dosing Regimens by Renal Function Group

| CLcr range for each renal function Group (mL/min/1.73 m$^2$) | ZTI-01 dosing regimes |
|---|---|
| >50 | 6 g q8 h |
| >40 to 50 | 4 g q8 h |
| >30 to 40 | 6 g loading dose followed by 3 g q8 h[a] |
| >10 to 30 | 6 g loading dose followed by 5 g q24 h[b] |

Note:
ZTI-01 infused over 1 hour
[a]3 g q8 h to be administered 8 h after 6 g loading dose
[b]5 g q24 h to be administered 24 h after 6 g loading dose Total-drug AUC values from 0 to 24 hours on Day 1 were calculated by numerical integration of the concentration-time profiles. Total-drug AUC:MIC ratios were calculated by dividing total-drug plasma AUC values by fixed MIC values based on the MIC distribution for fosfomycin against Enterobacteriaceae isolates (Flamm et al. Fosfomycin activity when tested against Gram-positive and Gram-negative US isolates collected by the SENTRY Antimicrobial Surveillance Program. *American Society of Microbiology Microbe* 2017, New Orleans, La. Jun. 1-5, 2017).

Non-Clinical PK-PD Targets for Efficacy

Total-drug plasma AUC:MIC ratio targets for Enterobacteriaceae efficacy evaluated, as shown in Table 14, were based on data from a neutropenic murine-thigh infection model (Lepak et al. Zavante Therapeutics, Inc. 00420 (Fosfomycin): In vivo pharmacodynamics of ZTI-01 (Fosfomycin for Injection) in the neutropenic murine thigh infection model against ESBL-positive *E. coli* (EC), carbapenem-resistant (CR) *K. pneumoniae* (KPN), and *P. aeruginosa* (PSA). *American Society of Microbiology Microbe* 2017, New Orleans, La. Jun. 1-5, 2017). Emphasis was placed on the assessment of the total-drug AUC:MIC ratio targets associated with net bacterial stasis.

TABLE 14

Summary of Total-Drug AUC:MIC Ratio Targets for *Enterobacteriaceae* Efficacy

| Bacterial reduction endpoint | Median total-drug AUC:MIC ratio |
|---|---|
| Net bacterial stasis | 19.1 |
| 1 log$_{10}$ CFU reduction from baseline | 41.6 |

Evaluation of PK-PD Target Attainment

Percent probabilities of PK-PD target attainment by MIC and overall (i.e., weighted over a MIC distribution for fosfomycin against Enterobacteriaceae) were determined. The MIC distribution for Enterobacteriaceae was based on 1,021 isolates collected from US medical centers, the MIC50 and MIC90 values for which were 4 and 16 mg/L, respectively.

Figure 6:
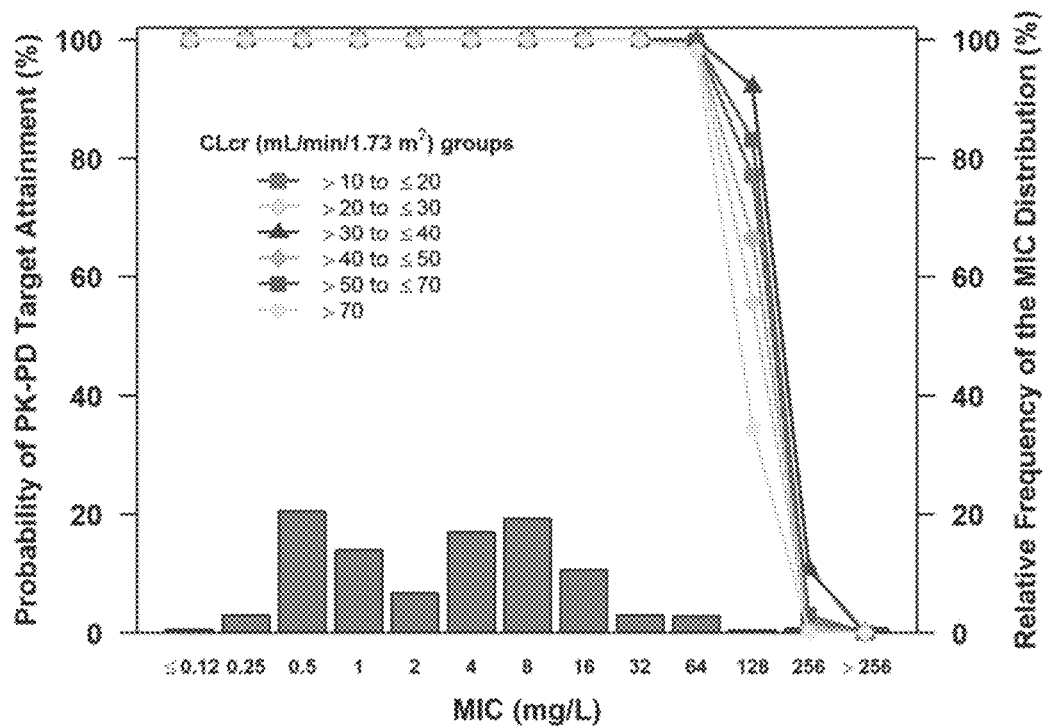
FIG. 6 depicts percent probabilities of PK-PD target attainment by MIC for each renal function group, overlaid on the fosfomycin MIC distribution for Enterobacteriaceae.

Results: Percent probabilities of PK-PD target attainment by MIC and overall among simulated patients by renal function group after administration of ZTI-01 dosing regimens are shown in Table 15. Percent probabilities of achieving the total-drug AUC:MIC ratio target associated with net bacterial stasis by MIC, overlaid on the fosfomycin MIC distribution for Enterobacteriaceae are shown in FIG. 6.

At a MIC value of 64 mg/L, percent probabilities of achieving the PK-PD target associated with net bacterial stasis were ≥98.3% across renal function groups. Overall percent probabilities of achieving the above-described PK-PD target were ≥98.0% across renal function groups.

TABLE 15

Percent Probabilities of PK-PD Target Attainment by MIC and Overall among Simulated Patients by Renal Function Group after Administration of ZTI-01 Dosing Regimens

| Endpoints for total-drug | | Percent probabilities of PK-PD target attainment by MIC across renal function group by among simulated patients | | | | | |
|---|---|---|---|---|---|---|---|
| AUC:MIC ratio targets | MIC (mg/L) | >10 to ≤ 20 (mL/min/ 1.73 m$^2$) | >20 to ≤ 30 (mL/min/ 1.73 m$^2$) | >30 to ≤ 40 (mL/min/ 1.73 m$^2$) | >40 to ≤ 50 (mL/min/ 1.73 m$^2$) | >50 to ≤ 70 (mL/min/ 1.73 m$^2$) | > 70 (mL/min/ 1.73 m$^2$) |
| Net bacterial stasis | 32 | 100 | 100 | 100 | 100 | 100 | 100 |
| | 64 | 99.8 | 99.5 | 100 | 99.7 | 99.9 | 98.3 |
| | 128 | 77.1 | 55.7 | 92.1 | 66.5 | 83.2 | 34.6 |
| | 256 | 1.9 | 0.4 | 10.7 | 0.9 | 3.0 | 0.1 |
| | Overall$^a$ | 98.2 | 98.1 | 98.4 | 98.2 | 98.3 | 98.0 |
| 1-log$_{10}$ CFU reduction | 32 | 99.8 | 99.1 | 99.9 | 99.5 | 99.9 | 97.3 |
| | 64 | 65.5 | 44.0 | 86.4 | 52.7 | 72.5 | 22.3 |
| | 128 | 0.7 | 0.1 | 5.8 | 0.2 | 1.3 | 0 |
| | 256 | 0 | 0 | 0 | 0 | 0 | 0 |
| | Overall$^a$ | 96.9 | 96.2 | 97.5 | 96.5 | 97.1 | 95.6 |

Note:
Shaded cells indicate percent probabilities of PK-PD target attainment by MIC ≥ 90%.
$^a$Based on data for 1,021 *Enterobacteriaceae* isolates collected from US medication centers as part of the 2105 SENTRY Antimicrobial Surveillance Program.
Conclusion: Together with clinical outcome data, results of these analyses will provide support for ZTI-01 dosing recommendations for patients with cUTI and fosfomycin susceptibility breakpoints for *Enterobacteriaceae*.

It will be appreciated that details of the foregoing embodiments, given for purposes of illustration, are not to be construed as limiting the scope of this invention. Although several embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

What is claimed is:

1. A dosing regimen for administering fosfomycin or a pharmaceutically acceptable salt thereof to a renally impaired patient in need of treatment wherein said renally impaired patient has an estimated creatinine clearance of >40 to ≤50 mL/min comprising administering 4 grams of fosfomycin or a pharmaceutically acceptable salt thereof intravenously every 8 hours.

2. A dosing regimen for administering fosfomycin or a pharmaceutically acceptable salt thereof to a renally impaired patient in need of treatment wherein said renally impaired patient has an estimated creatinine clearance of >30 to ≤40 mL/min comprising administering 6 grams of fosfomycin or a pharmaceutically acceptable salt thereof intravenously once, then with 3 grams of fosfomycin or a pharmaceutically acceptable salt thereof intravenously every 8 hours.

3. A dosing regimen for administering fosfomycin or a pharmaceutically acceptable salt thereof to a renally impaired patient in need of treatment wherein said renally impaired patient has an estimated creatinine clearance of >20 to ≤30 mL/min comprising administering a first dose of 6 grams of fosfomycin or a pharmaceutically acceptable salt thereof intravenously and a second dose of 5 grams of fosfomycin or a pharmaceutically acceptable salt thereof intravenously every 24 hours.

4. The method of claim 1, 2, or 3, wherein the duration of treatment is between about 7 days and about 14 days.

5. A dosing regimen for administering fosfomycin or a pharmaceutically acceptable salt thereof to a renally impaired patient in need of treatment wherein said renally impaired patient has an estimated creatinine clearance of >40 to ≤50 mL/min or of >30 to ≤40 mL/min comprising administering 4 grams of fosfomycin or a pharmaceutically acceptable salt thereof intravenously every 8 hours if said renally impaired patent has an estimated creatinine clearance of >40 to ≤50 mL/min or administering 6 grams of fosfomycin or a pharmaceutically acceptable salt thereof intravenously once, then with 3 grams of fosfomycin or a pharmaceutically acceptable salt thereof intravenously every 8 hours if said renally impaired patient has an estimated creatinine clearance of >30 to ≤40 mL/min.

6. A dosing regimen for administering fosfomycin or a pharmaceutically acceptable salt thereof to a renally impaired patient in need of treatment wherein said renally impaired patient has an estimated creatinine clearance of >40 to ≤50 mL/min or of >30 to ≤40 mL/min or of >20 to ≤30 mL/min comprising administering 4 grams of fosfomycin or a pharmaceutically acceptable salt thereof intravenously every 8 hours if said renally impaired patent has an estimated creatinine clearance of >40 to ≤50 mL/min or administering 6 grams of fosfomycin or a pharmaceutically acceptable salt thereof intravenously once, then with 3 grams of fosfomycin or a pharmaceutically acceptable salt thereof intravenously every 8 hours if said renally impaired patient has an estimated creatinine clearance of >30 to ≤40 mL/min or administering 6 grams of fosfomycin or a pharmaceutically acceptable salt thereof intravenously once, then with 5 grams of fosfomycin or a pharmaceutically acceptable salt thereof intravenously every 24 hours if said renally impaired patient has an estimated creatinine clearance of >20 to ≤30 mL/min.

7. The method of claim 5 or 6, wherein the duration of treatment is between about 7 days and about 14 days.

8. A dosing regimen for administering fosfomycin or a pharmaceutically acceptable salt thereof to a renally impaired patient in need of treatment wherein the renally impaired patient is diagnosed with a cUTI and has an estimated creatinine clearance of >10 to 20 mL/min, the dosing regimen comprising administering to the patent 6 grams of fosfomycin or a pharmaceutically acceptable salt thereof intravenously once, followed by a second administration of 5 grams of fosfomycin or a pharmaceutically acceptable salt thereof intravenously every 24 hours.

9. The method of claim 8, wherein the duration of treatment is between about 7 days and about 14 days.

* * * * *